United States Patent [19]

Noda et al.

[11] Patent Number: 5,129,912
[45] Date of Patent: Jul. 14, 1992

[54] DEVICE AND METHOD FOR APPLYING SUTURE

[75] Inventors: Wayne A. Noda, Mission Viejo; Paul Lubock, Laguna Niguel, both of Calif.

[73] Assignee: Laparomed Corporation, Irvine, Calif.

[21] Appl. No.: 638,887

[22] Filed: Jan. 7, 1991

[51] Int. Cl.⁵ ............................................. A61B 17/00
[52] U.S. Cl. ..................................... 606/139; 606/147; 606/148; 289/1.2; 289/1.5; 289/17
[58] Field of Search ...................... 289/1.5, 1.2, 2, 17; 606/139, 145, 147, 148, 113, 144

[56] References Cited

U.S. PATENT DOCUMENTS

| | | | |
|---|---|---|---|
| 1,856,721 | 5/1932 | Nagelmann | 606/145 |
| 2,227,270 | 12/1940 | Moore | 606/113 |
| 2,856,933 | 10/1958 | Hildebrand et al. | 606/113 |
| 3,580,256 | 5/1971 | Wilkinson | 289/1.5 |
| 3,871,379 | 3/1975 | Clarke | 606/148 |
| 4,345,599 | 8/1982 | McCarrell | 606/113 |
| 4,602,635 | 7/1986 | Mulhollan et al. | 606/144 |
| 4,641,652 | 2/1987 | Hutterer et al. | 606/148 |
| 4,760,848 | 8/1988 | Hasson | 606/206 |
| 4,923,461 | 5/1990 | Caspari et al. | 606/146 |

Primary Examiner—Stephen C. Pellegrino
Assistant Examiner—Gary Jackson
Attorney, Agent, or Firm—Townsend and Townsend

[57] ABSTRACT

A suture applier comprises a shaft having proximal and distal ends and carrying a length of suture along its axis. The suture has a surgical needle at its distal end and a knotted loop formed proximally of the needle. The knotted loop is carried at the distal end of the shaft, and a slidable handle is provided at the proximal end for applying axial tension on the suture. In this way, the needle may be used to suture a wound in tissue and may be tied by passing the needle through the knotted loop and closing the loop by pulling on the slidable handle.

27 Claims, 5 Drawing Sheets

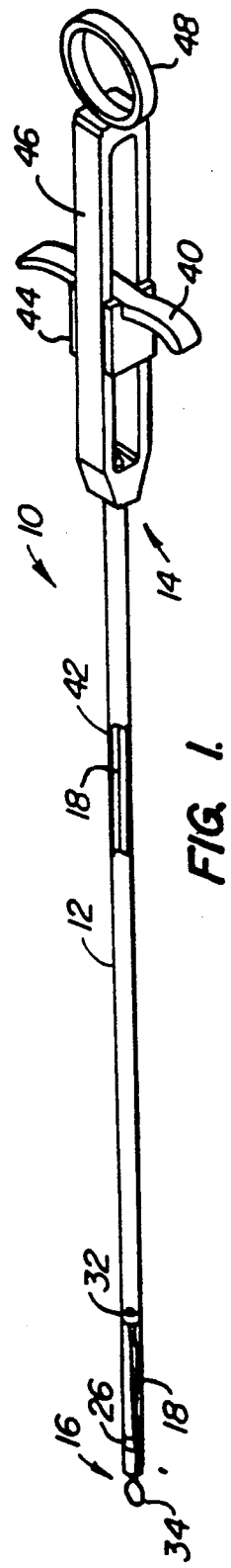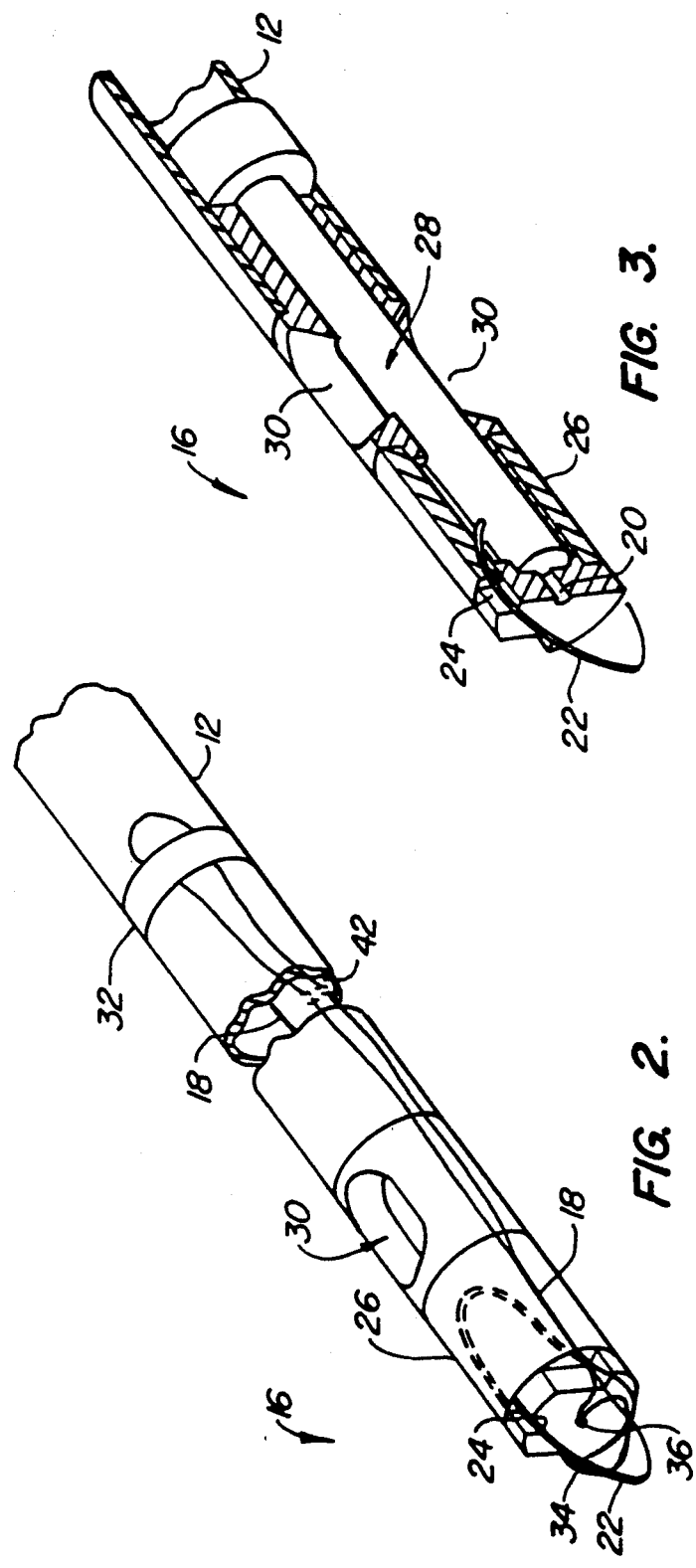

DEVICE AND METHOD FOR APPLYING SUTURE

BACKGROUND OF THE INVENTION

1. Field of the Invention

The present invention relates generally to the structure and use of surgical instruments, and more particularly, to a device and method for applying and knotting suture in locations having limited access.

Least invasive surgical (LIS) techniques, such as laparoscopic, endoscopic, and arthroscopic surgery, are generally performed through small incisions using specialized instruments to perform desired surgical procedures. Usually, the instruments are introduced through a tube, such as a cannula, while the physician observes manipulation of the instruments through specialized imaging equipment, such as laparoscopes, endoscopes, and arthroscopes. Such LIS techniques offer significant advantages over conventional "open" surgical procedures. In particular, the LIS techniques are usually less traumatic, require a shorter recovery time, and are less costly than the corresponding conventional surgical techniques.

While such LIS procedures have been very successful, improvements in the instruments and techniques which are employed will enhance the efficiency of those procedures which are presently performed and potentially extend the application of LIS techniques to new surgical procedures. In particular, it would be desirable to improve the design of LIS instruments so that they are more readily manipulable, better able to perform specific tasks, less likely to expose the patient to inadvertent injury, and the like.

Of particular interest to the present invention are LIS instruments for applying and tying suture at remote locations. Heretofore, the most common approaches for tying suture have been to manually tie a knot in the free ends of the suture outside of the cannula and to push the knot forward through the cannula using a rod or to tie the knot in situ using instruments. While workable, such techniques are time consuming, limit the type of knot which can be formed, and usually require at least two tying steps to form a tight knot. Thus, it would be desirable to provide improved methods and instruments for applying and tying suture at remote locations.

One improvement which has been proposed is the use of preformed knotted loops in suture. Such knotted loops allow the suture to be tied by passing a free end of the suture through the loop and tightening the loop on the suture after the wound has been closed. Such a technique and an instrument for performing the technique are described in U.S. Pat. No. 4,760,848, described further hereinbelow. The instrument described in the '848 patent, however, is deficient in certain respects. In particular, the instrument must release the knotted loop prior to passing the free end of the suture therethrough. Thus, the loop can be temporarily lost by the physician, making tying of the knot problematic. The instrument described further lacks any capability for tightening the knotted loop to facilitate tying of the free end of the suture. It would be desirable if the instrument carrying the loop were able to hold the knotted loop during the entire procedure and to tighten the knotted loop without the need to employ a separate instrument.

2. Description of the Relevant Art

U.S. Pat. No. 4,760,848, describes a surgical instrument having a pair of jaws at a distal end of a tube. The jaws may be used for carrying a surgical needle which is attached to a length of suture. The suture may have a preformed loop with a slip knot that allows the suture to be tied by passing the needle back through the loop. U.S. Pat. Nos. 4,923,461 and 4,602,635, describe surgical knotting devices where a knot is tied externally and the knot pushed forward to the tissue being sutured. Other remote surgical knotting devices are described in U.S. Pat. Nos. 4,641,652 and 3,871,379.

SUMMARY OF THE INVENTION

According to the present invention, a suture applier comprises a shaft having proximal and distal ends. The shaft carries a length of suture having proximal and distal ends, a surgical needle attached at the distal end, and a knotted loop disposed proximally of the needle. The suture is carried on the shaft, usually in an axial passageway formed through the shaft, with the surgical needle and knotted loop extending outward from the distal end of the shaft. A means is provided on the shaft for securing and applying axial tension on a proximal portion of the suture, while a further means is provided on the distal end of the shaft for holding the knotted loop against such axial tension. The holding means will typically comprise a port formed at the distal end of the axial passageway, where the port is sized to engage the knot in the knotted loop formed in the suture. In this way, the knotted loop can be closed using the suture applier alone by tensioning or pulling against the proximal end of the suture.

In a specific embodiment of the present invention, the means for applying tension is a handle slidably received in an axial track attached to the proximal end of the shaft. The tension applying means may further include a ring at its proximal end, allowing the user to apply tension using a pair of fingers which engage the handle in opposition to the thumb which is held within the ring. In this way, the device can be manipulated and actuated using a single hand.

In further specific embodiments, various means are provided for detachably securing the surgical needle and/or a free end of the knotted loop on the shaft. In this way, the needle and loop may be secured while the shaft is introduced or removed, typically through a cannula. Also, the needle may be held and the suture tensioned to facilitate trimming of the suture tails after the suture is tied.

In another aspect of the present invention, a length of suture having a surgical needle at a distal end thereof and a knotted loop formed proximally of the surgical needle is provided. The knotted loop is formed with a particular slip knot as illustrated in FIGS. 5A–5E. This particular slip knot has been found to facilitate tightening and closing of the knotted loop while providing a highly secure final knot in the suture.

According to the method of the present invention, the distal end of the shaft is introduced proximate a wound to be sutured, typically through a cannula. The distal end of the shaft carries a preformed, knotted loop in a length of suture. A surgical needle at the distal end of the length of suture is passed through the tissue across the wound while the knotted loop remains on the distal end of the shaft. The surgical needle is then passed through the knotted loop to form a secondary loop in the suture, while the knotted loop still remains on the distal end of the device. The knotted loop can then be tightened about the suture by applying axial tension on a proximal portion of the suture to close the knotted loop against the distal end of the shaft. The secondary loop is closed by applying tension on the distal end of the suture to bind the wound. Preferably, axial tension on the proximal end of the suture is applied using a handle formed on the shaft itself. Usually, the free end of the knotted loop and the surgical needle are retained on the shaft while the shaft is introduced, and the needle is subsequently manipulated using a separate needle holder. The needle can be replaced on the shaft after the suture is tied to facilitate trimming of the tail ends of the suture.

BRIEF DESCRIPTION OF THE DRAWINGS

FIG. 1 is a perspective view of a suture applier constructed in accordance with the principles of the present invention.

FIG. 2 is a detailed view of the distal end of the suture applier of FIG. 1.

FIG. 3 is a cross-sectional view of the distal end of the suture applier of FIG. 1.

DESCRIPTION OF THE SPECIFIC EMBODIMENTS

Figure 4:
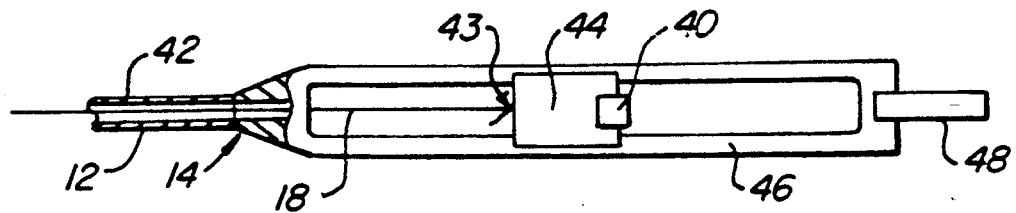
FIG. 4 is a side-elevational view of the proximal end of the suture applier of FIG. 1.

The device and method of the present invention are useful for applying and tying suture in a wide variety of surgical procedures, being most useful where the suturing is to be performed in regions with limited accessibility. The present invention will find its greatest use in the performance of laparoscopic, arthroscopic, and endoscopic surgery where the suturing device is introduced and manipulated through relatively narrow cannulas, typically having a diameter of five millimeters or less. Particular procedures which may be performed using the present invention include coapting tissue, where the opposed lips of a wound are joined together after an accidental tear or dissection; ligating vessels or ducts where the suture is passed around a structure and cinched sufficiently tight to occlude the structure so that it can be transected without leakage; anchoring a cannula within a vessel or duct by suturing around the periphery; repairing an access hole left after the removal of a cannula or catheter; retracting of obstructing tissue or organs by cinching the suture loop around said tissue or organ; forming a continuous or running stitch after an initial knot is formed using the knotted loop; repair of bleeding blood vessels; and securing of grafts for hernia repair, anti-adhesion, and the like. Other uses within the spirit of the present invention will occur to those skilled in the art.

The device of the present invention will include a preselected length of suture having a surgical needle attached at one end and a knotted loop formed at a location proximal to the surgical needle. The length of the suture may vary widely, typically being from about 30 to 100 cm, more typically being from about 40 to 60 cm. The preformed knotted loop will typically be spaced-proximally of the surgical needle by a distance in the range from about 4 to 20 cm, usually being in the range from about 10 to 15 cm. The suture may be formed from any conventional surgical suture material, such as silk, wire, gut, and the like. The surgical needle will be a conventional needle, typically having a curved profile to facilitate stitching of a wound using conventional needle holders or forceps.

The loop in the suture will be formed by tying a slip knot in the suture to leave a loop having a target hole therethrough. The diameter of the loop is not critical, typically being in the range from about 5 to 20 mm, more typically being in the range from about 8 to 15 mm.

The knot which forms the loop will be a slipknot, such as a conventional hangman's knot. A particular slipknot which has been found to be suitable for use in the present invention is discussed and illustrated hereinafter. The knot allows the loop to be cinched tight about the free distal end of the suture which is passed back therethrough, forming a particularly secure final knot in the tissue. The loop can be closed by pulling on at least one of the suture ends while the knot is held in place.

The device of the present invention will comprise a shaft having proximal and distal ends. The shaft may have any cross-sectional (peripheral) shape, usually having a round circumference, i.e., being a rod or a cylinder. The diameter of the shaft is not critical, but will usually be sufficiently small to allow passage through a cannula, typically being five millimeters or less.

The shaft will include means for holding the length of suture in axial alignment therewith. Typically, the holding means will comprise an axial passageway extending from the proximal to distal end of the shaft, but could also consist of external structure on the shaft for holding the suture in the desired alignment.

The shaft will further have means for securing and applying an axial tension to a proximal end of the suture which is being held on the shaft. Usually, the tensioning means will comprise a slidable handle which allows the user to manually apply the desired axial tension. Other mechanisms, such as levers, scissors, and the like, could be used to either manually or automatically apply the desired tension, but such structures are generally more complex and less desirable than use of the slidable handle.

The knotted loop and needle on the length of suture will extend from the distal end of the shaft, and a means will be provided at the distal end of the shaft for holding the loop against the distal tip of the shaft as axial tension is applied, e.g., using the slidable handle just described. Typically, the means for holding the knotted loop will comprise a port or orifice formed in the distal tip of the shaft, where the diameter of the opening is selected to permit free passage of the suture, but block passage of the knot in the suture, i.e., the port or orifice will have a diameter larger than the suture but smaller than the knot. Thus, because of the nature of the slipknot, pulling on the proximal end of the suture will close the loop while the knot is held stationary against the distal tip of the shaft.

Conveniently, the shaft will include means at or near its distal end for carrying the needle to facilitate introduction and removal of the device through a cannula or other limited access port. The shaft will usually also include means for detachably securing the free end of the preformed loop as well as the region of suture between the loop and the surgical needle which would otherwise be loose and subject to entanglement. The means for securing the needle will also be useful for tensioning the distal end of the suture as the suture is trimmed after tying. Specific structures for providing such securing means are described in detail hereinafter in reference to the figures.

The suture applier of the present invention will usually be a single-use device which, after fabrication, is sterilized and placed in sterile packaging. Alternatively, it would be possible to reuse the shaft portion of the device (after sterilization) by replacing the length of suture having the preformed knot and surgical needle. Thus, the present invention includes the suture needle. Thus, the present invention includes the suture itself having the particular slip knot which is described hereinafter, usually present in sterile packaging.

Referring now to FIGS. 1-4, a suture applying device 10 constructed in accordance with the principles of the present invention will be described. The suture applier 10 includes a shaft 12 having a proximal end 14 and a distal end 16. A length of suture 18 extends from the shaft 12 through a port 20 (FIG. 3) at the distal end of shaft. Surgical needle 22 is attached to a distal end of suture 18 and is removably secured through a slot 24 and into a first elastic band 26 and silicone rubber insert tube 28. It will be appreciated that the surgical needle 22 can be pulled out through port 24 by pulling on the protruding end, as will be described in more detail hereinafter.

A pair of opposed access ports 30 are formed on opposite sides of the shaft 12 a short distance proximal from the distal end 16. The ports 30 are intended to provide a means for securing the needle as the device is withdrawn from use, as will be described in more detail hereinafter. The needle 22 is simply passed through one of the two ports 30 and penetrated into the silicone rubber tube 28 where it will be retained until it is removed.

A second elastic band 32 is formed a short distance proximally from the distal tip of the shaft 12. The distance is usually in the range from about 2 to 10 cm, more usually being in the range from about 5 to 8 cm. The elastic band 32 is intended to allow the length of suture 18 between a knotted loop 34 and the surgical needle 22 to be detachably secured to the shaft 12.

As best observed in FIG. 2, the knotted loop 34 includes a slipknot 36 (as will be described in more detail hereinafter) which is generally held at the distal port 20. The loop 34 will thus extend from the distal end of the shaft 12, as best observed in FIG. 1. The loop 34, however, may be detachably secured (folded back) beneath the elastic band 26, as illustrated in broken line in FIG. 2.

A slidable handle 40 is located at the proximal end 14 of the shaft 12 in order to provide an axial tension on the suture 18. Suture 18 extends in a proximal direction from port 20 through an axial passage 42 in tube 12 and is secured at its proximal end 43 to a sliding block 44 which is attached to the handle 40. Sliding block 44 is capable of axially translating within a track defined by an open frame 46 which is attached to the proximal end of the tube 12. A thumb ring 48 is conveniently provided at the proximal end of the frame 46. In this way, the user can hold the suture applier 10 in one hand with the user's thumb in thumb ring 48 and the index finger and forefinger engaged in opposition to the thumb against the handle 40. Tension may be applied on suture 18 then by simply pulling on the handle 40 with the fingers against to the thumb. This structure allows very precise control on the tension and facilitates closing loop 34 to form a tight knot, as described in more detail hereinafter.

Figure 4A:
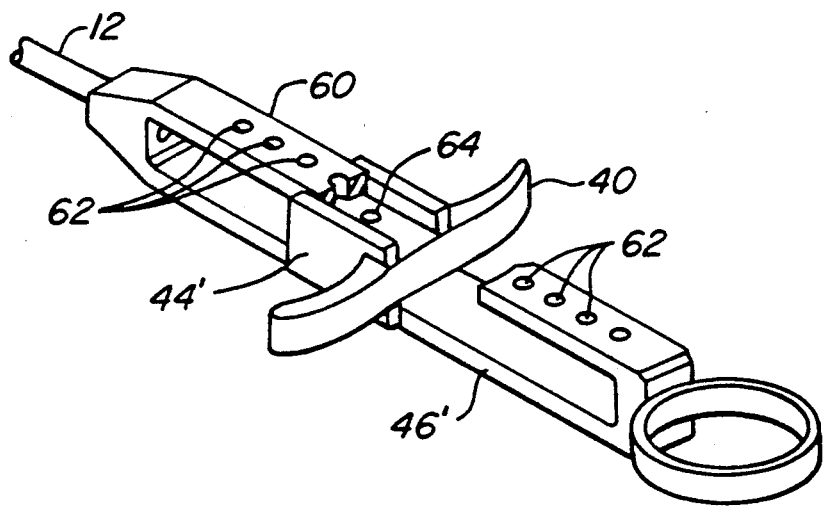
FIG. 4A is a detailed perspective view of the proximal end of an alternate embodiment of a suture applier constructed in accordance with the principles of the present invention.

An alternate embodiment of the proximal end of the suture applier is illustrated in FIG. 4A. The proximal end includes a slidable handle 40' attached to sliding block 44' which is slidably received in a track defined by open frame 46'. The track 46' includes a top rail 60 having a plurality of spaced-apart detent holes 62 formed therein. A spring-loaded ball 64 is located on sliding block 44' and aligned so that it can selectively engage the detent holes 62 as the handle 40 is translated forward and backward in the track 46'. The detents allow the handle to be "ratcheted" in the proximal direction so that the treating physician can incrementally apply tension to the suture. The detents will hold the handle at a desired level of tension, reducing muscle fatigue in the physician's hand.

Figure 5A:
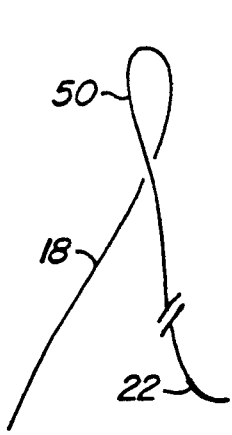
FIGS. 5A-5E illustrate the steps for tying the preferred slipknot for forming the knotted loop in the suture of the present invention.
Figure 5B:
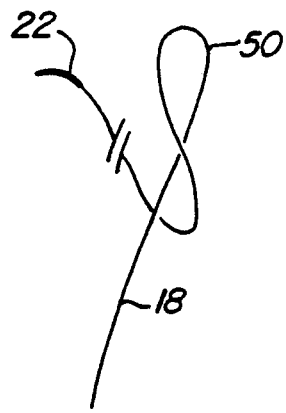
Figure 5C:
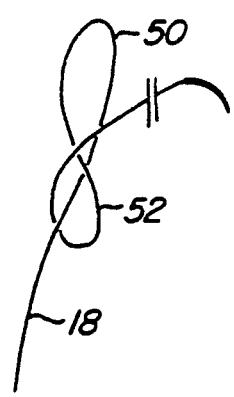
Figure 5D:
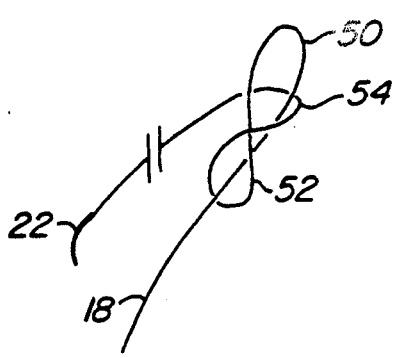
Figure 5E:
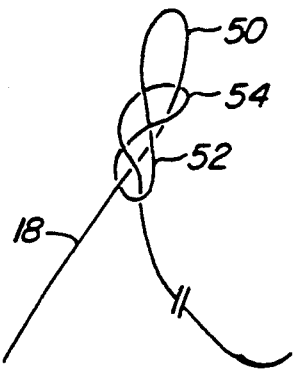

Referring now to FIGS. 5A-5E, the steps for forming the preferred slipknot 36 of the present invention will be described. The distal end of suture 18 having the attached surgical needle 22 is doubled over to form a first loop 50, as illustrated in FIG. 5A. The needle 22 is then pulled back around the proximal portion of suture 18 (FIG. 5B) and then brought around to cross over the front of the suture 18 to form a second loop 52 (in a figure eight pattern with first loop 50), with the proximal length of suture 18 passing through the second loop 52. The needle 22 is next brought around the back of the emerging knot structure to form a third loop 54 (FIG. 5D) which encircles the crossover region between loops 50 and 52. The needle is then brought through the lower loop 52 in order to complete the slipknot structure.

Figure 6:
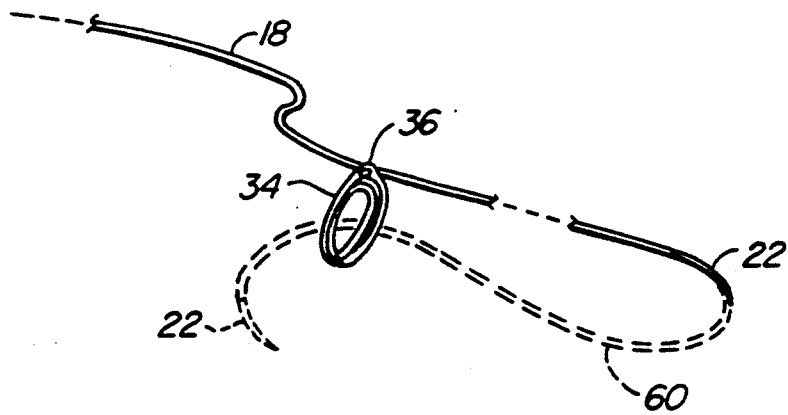
FIG. 6 illustrates a length of suture having the preferred slipknot and loop formed therein with a surgical needle at its distal end.

Suture 18 having loop structure 34 and slipknot 36 therein is illustrated in FIG. 6. It will be appreciated that the loop structure 34 corresponds to the loop 50 formed as illustrated in FIGS. 5A-5E which has been doubled over to form a double loop. The slipknot 36 is formed from loops 52 and 54, and the proximal end (i.e., to the left in FIG. 6) of the suture 18 can be pulled through the slip knot to tighten and close the loop 34.

To form the final suture knot according to the present invention, the needle 22 is passed through the interior of loop 34, as illustrated in broken line in FIG. 6. The loop 34 is then tightened by pulling on the proximal end of suture 18 as just described. A secondary loop 60 which is formed when the needle 22 is passed through the first loop 34 may then be tightened by pulling on the distal or needle end of the suture 18. As described in more detail hereinafter, it is this secondary loop which actually forms the suture stitch in the wound being closed.

Figure 7A:
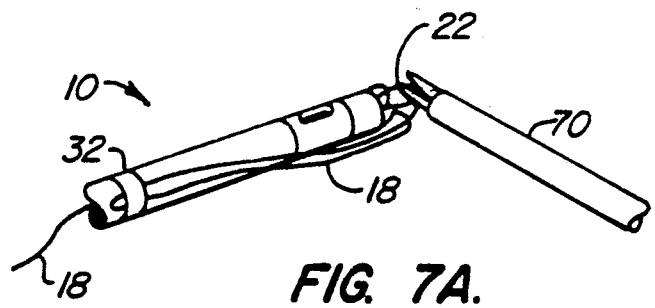
FIGS. 7A-7G illustrate the method of the present invention using the suture applier of FIG. 1 to suture and tie a wound in tissue.
Figure 7B:
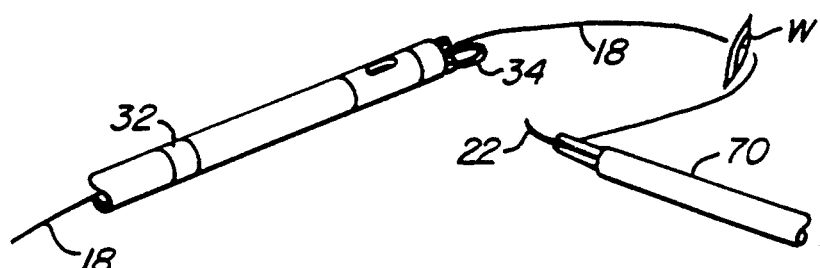
Figure 7C:
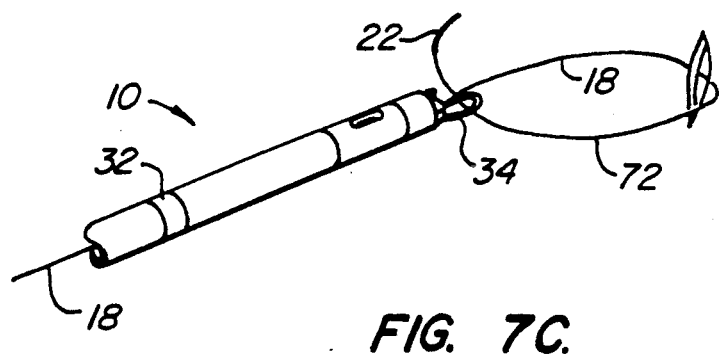

Referring now to FIGS. 7A-7G, the method of the present invention will be described. Initially, the suture applier 10 is removed from its sterile packaging to the sterile field using standard aseptic techniques. The suture applier 10 is then introduced through a cannula or other access tube to a region of interest, typically near a wound to be sutured. A needle holder 70 is introduced to the same region through a second cannula or other access tube and the needle 22 is grasped and removed from its port on the suture applier 10 (FIG. 7A).

After removing the needle 22, the excess length of suture 18 between the loop 34 and the needle is removed from elastic band 32, and the needle is then passed through the tissue on either side of a wound W (FIG. 7B) in a conventional manner. The needle 22 is then brought through the loop 34 (FIG. 7C) to form a secondary loop 72.

Figure 7D:
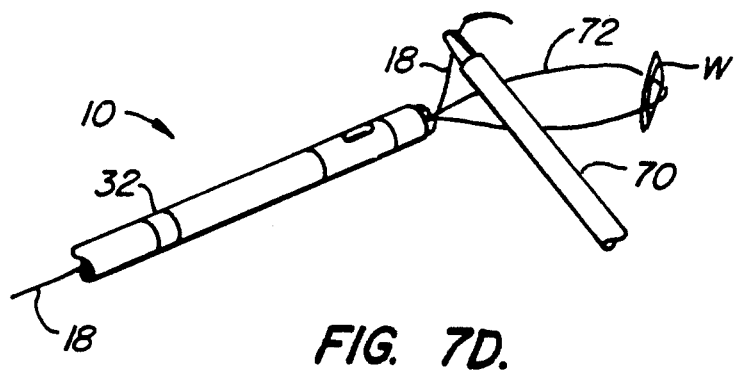
Figure 7E:
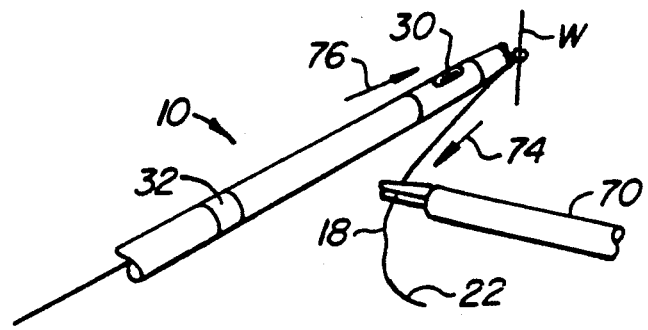
Figure 7F:
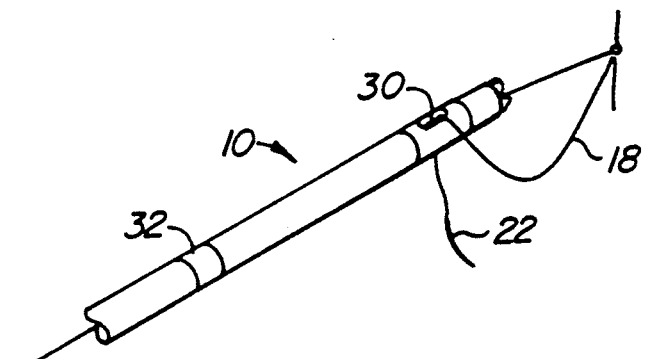

After forming the secondary loop 72, the distal end of suture 18 is held in place with the needle holder 70, and the handle 40 is used to apply tension on the proximal end of suture 18 in order to close loop 34 about the suture 18 passing therethrough (FIG. 7D). The secondary loop 72 is then closed by pulling on the distal end of suture 18 in the direction shown by arrow 74 (FIG. 7E), while the suture applier 10 is used to apply a counter force in the direction of arrow 76. After the secondary loop 72 has been tightened to close the wound W, the (primary) loop 34 may be further tightened by applying additional tension on the handle 40. After the loop 34 is tightened to a sufficient degree, tension on the suture 18 may be released (FIG. 7F), and the needle 22 will be passed through the needle ports 30. The tail ends of suture 18 extending from the tied suture knot will then be clipped (conveniently using the applier 10 to pull back on the tail ends so that they can be cut using conventional scissors), and the suture applier 10 may be removed through the cannula with the needle being carried out with the suture applier.

Figure 7G:
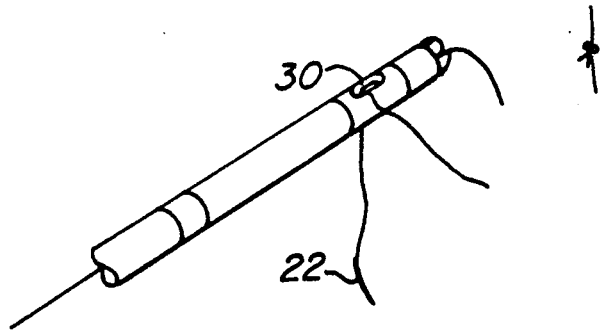

A continuous suture may be formed by securing a knot as described above with reference to FIGS. 7A through 7E, but proceeding with additional stitches prior to trimming the suture, as illustrated in FIG. 7G. The continuous stitch is terminated by performing an instrument tie after the final stitch is thrown, in a conventional manner. Retrieval of the instrument is performed in the same manner as described with reference to FIG. 7G.

Although the foregoing invention has been described in detail for purposes of clarity of understanding, it will be obvious that certain modifications may be practiced within the scope of the appended claims.

What is claimed is:

1. A suture applier comprising:
   a shaft having proximal and distal ends;
   a length of suture having proximal and distal ends, a surgical needle secured to the distal end of the suture, and a knotted loop in the suture spaced proximally from the needle, wherein said suture is axially aligned with the shaft and wherein said surgical needle and knotted loop extend from the distal end of the shaft;
   means at the proximal end of the shaft for securing and selectively applying axial tension on the proximal end of the suture; and
   means responsive to tension on the suture for holding the knotted loop at the distal end of the shaft.

2. A suture applier as in claim 1, wherein the means for securing and selectively applying axial tension includes an axially aligned track, a handle slidably received in said track, and means on the handle for retaining the proximal end of the suture.

3. A suture applier as in claim 1, further comprising means at the distal end of the shaft for removably securing the surgical needle.

4. A suture applier as in claim 3, wherein the means for removably securing the surgical needle comprises a port in the distal tip of the shaft having penetrable material behind said port.

5. A suture applier as in claim 4, further comprising an additional port in side wall of the shaft having penetrable material behind said port, whereby the surgical needle can be secured after use and the suture can be tensioned to facilitate trimming of the tail ends after the suture is tied.

6. A suture applier as in claim 1, further comprising means at the distal end of the shaft for detachably securing a free end of the knotted loop.

7. A suture applier as in claim 6, wherein said means for detachably securing a free end of the knotted loop is an elastic band.

8. A suture applier as in claim 7, further comprising a second elastic band spaced proximally from the first for detachably securing a portion of the suture between the surgical needle and the knotted loop.

9. A suture applier as in claim 1, wherein the knotted loop includes a slip knot formed as illustrated in FIGS. 5A to 5E.

10. A suture applier comprising:
    a shaft having a proximal end, a distal end, an axial passage therethrough, and a port at the distal end of the axial passage;
    a length of suture having a proximal end, a distal end, a surgical needle at the distal end of the suture, and a knotted loop in the suture spaced proximally from the needle, said suture being slidably disposed in the axial passage with the surgical needle and knotted loop extending from the port at the distal end of the axial passage; and
    means at the proximal end of the shaft for securing and selectively applying axial tension on the proximal end of the suture, whereby the knotted loop may be held against the port and closed by applying such tension.

11. A suture applier as in claim 10, wherein the means for securing and selectively applying axial tension includes an axially aligned track, a handle slidably received in said truck, and means on the handle for retaining the proximal end of the suture.

12. A suture applier as in claim 10, further comprising means at the distal end of the shaft for removably securing the surgical needle.

13. A suture applier as in claim 12, wherein the means for removably securing the surgical needle comprises a port in the distal tip of the shaft having penetrable material behind said port.

14. A suture applier as in claim 13, further comprising an additional port in side wall of the shaft having penetrable material behind said port, whereby the surgical needle can be secured after use and the suture can be tensioned to facilitate trimming of the tail ends after the suture is tied.

15. A suture applier as in claim 10, further comprising means at the distal end of the shaft for detachably securing a free end of the knotted loop.

16. A suture applier as in claim 15, wherein said means for detachably securing a free end of the knotted loop is an elastic band.

17. A suture applier as in claim 16, further comprising a second elastic band spaced proximally from the first for detachably securing a portion of the suture between the surgical needle and the knotted loop.

18. A suture applier as in claim 10, wherein the knotted loop includes a slip knot formed as illustrated in FIGS. 5A to 5E.

19. A sterilized length of suture having a proximal end, a distal end, and a surgical needle secured to the distal end, wherein a loop is preformed with a slip knot at a location proximal of the surgical needle, wherein said slip knot is formed as illustrated in FIGS. 5A to 5E.

20. A sterilized length of suture as in claim 19, which is disposed in sterile packaging.

21. A method for suturing a wound in tissue, said method comprising:
introducing the distal end of a shaft proximate said wound, wherein said distal end carries a preformed knotted loop in a length of suture;
passing a surgical needle at a distal end of the suture through the tissue across the wound while the knotted loop remains on the distal end of the shaft;
passing the surgical needle through the preformed knotted loop to form a secondary loop in the suture while the knotted loop remains on the distal end of the device;
applying axial tension on a proximal portion of the suture to close the knotted loop against the distal end of the shaft; and
applying tension on a distal portion of the suture to close the secondary loop and to bind the wound.

22. A method as in claim 21, wherein the shaft is introduced through a trocar.

23. A method as in claim 22, wherein a free end of the knotted loop is retained on the shaft while the shaft is introduced through the trocar.

24. A method as in claim 22, wherein the surgical needle is retained on the shaft while the shaft is introduced through the trocar.

25. A method as in claim 21, wherein the surgical needle is passed through the tissue and through the knotted loop using a needle holder.

26. A method as in claim 21, wherein axial tension is applied on the proximal portion of the suture using a handle which is slidably attached to the shaft.

27. A method as in claim 21, wherein tension is applied on the distal portion of the suture using a needle holder.

* * * * *

REEXAMINATION CERTIFICATE (3971st)

United States Patent
Noda et al.

[11] B1 5,129,912
[45] Certificate Issued Jan. 11, 2000

[54] DEVICE AND METHOD FOR APPLYING SUTURE

[75] Inventors: Wayne A. Noda, Mission Viejo; Paul Lubock, Laguna Niguel, both of Calif.

[73] Assignee: Urohealth Systems, Inc., Costa Mesa, Calif.

Reexamination Request:
No. 90/004,710, Jul. 31, 1997

Reexamination Certificate for:
Patent No.: 5,129,912
Issued: Jul. 14, 1992
Appl. No.: 07/638,887
Filed: Jan. 7, 1991

[51] Int. Cl.$^7$ .................................. A61B 17/00
[52] U.S. Cl. .............. 606/139; 606/147; 606/148; 289/1.2; 289/1.5; 289/17
[58] Field of Search ........................ 606/139, 147, 606/148

[56] References Cited

U.S. PATENT DOCUMENTS 2,012,776  8/1935  Roeder ........................ 606/144

FOREIGN PATENT DOCUMENTS 912619  10/1953  Germany.

*Primary Examiner*—Gary Jackson

[57] ABSTRACT

A suture applier comprises a shaft having proximal and distal ends and carrying a length of suture along its axis. The suture has a surgical needle at its distal end and a knotted loop formed proximally of the needle. The knotted loop is carried at the distal end of the shaft, and a slidable handle is provided at the proximal end for applying axial tension on the suture. In this way, the needle may be used to suture a wound in tissue and may be tied by passing the needle through the knotted loop and closing the loop by pulling on the slidable handle.

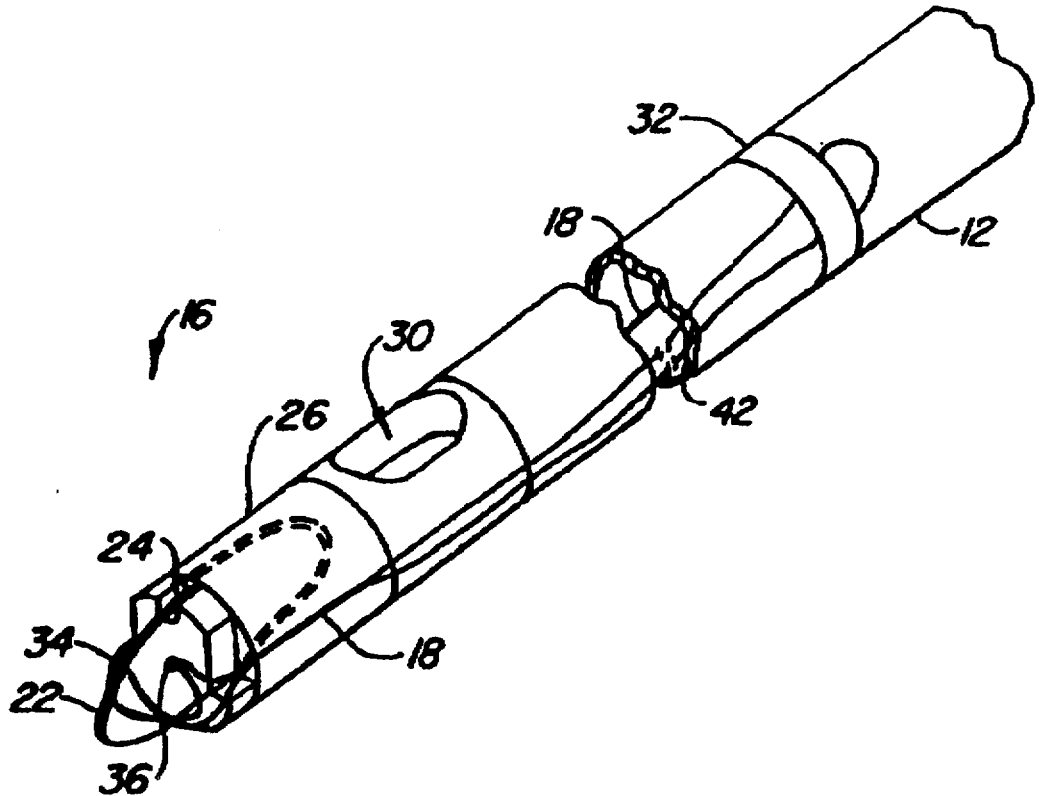

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10–20 is confirmed.

Claims 1, 2, 9 and 21–27 are cancelled.

Claims 3 and 6 are determined to be patentable as amended.

Claims 4, 5, 7 and 8, dependent on an amended claim, are determined to be patentable.

3. A suture applier [as in claim 1, further] comprising:
*a shaft having proximal and distal ends;*
*a length of suture having proximal and distal ends, a surgical needle secured to the distal end of the suture, and a knotted loop in the suture spaced proximally from the needle, wherein said suture is axially aligned with the shaft and wherein said surgical needle and knotted loop extend from the distal end of the shaft;*
*means at the proximal end of the shaft for securing and selectively applying axial tension on the proximal end of the suture;*
*means responsive to tension on the suture for holding the knotted loop at the distal end of the shaft; and*
means at the distal end of the shaft for removably securing the surgical needle.

6. A suture applier [as in claim 1, further] comprising:
*a shaft having proximal and distal ends;*
*a length of suture having proximal and distal ends, a surgical needle secured to the distal end of the suture, and a knotted loop in the suture spaced proximally from the needle, wherein said suture is axially aligned with the shaft and wherein said surgical needle and knotted loop extend from the distal end of the shaft;*
*means at the proximal end of the shaft for securing and selectively applying axial tension on the proximal end of the suture;*
*means responsive to tension on the suture for holding the knotted loop at the distal end of the shaft; and*
means at the distal end of the shaft for detachably securing a free end of the knotted loop.

* * * * *